United States Patent [19]

Scheinberg

[11] 4,071,037

[45] * Jan. 31, 1977

[54] PREPARATION AND METHOD OF USE OF ENZYME EFFECTIVE FOR CONVERSION AND DETECTION OF CARBON MONOXIDE

[76] Inventor: Israel Herbert Scheinberg, 5447 Palisade Ave., Bronx, N.Y. 10471

[*] Notice: The portion of the term of this patent subsequent to Sept. 28, 1993, has been disclaimed.

[21] Appl. No.: 715,479

[22] Filed: Aug. 18, 1976

Related U.S. Application Data

[63] Continuation-in-part of Ser. No. 659,199, Feb. 19, 1976, Pat. No. 3,982,897, which is a continuation-in-part of Ser. No. 292,011, Sept. 25, 1972, which is a continuation-in-part of Ser. No. 151,153, June 8, 1971, abandoned, and Ser. No. 102,869, June 8, 1971, Pat. No. 3,693,327, which is a continuation-in-part of Ser. No. 85,087, Oct. 29, 1970, abandoned.

[51] Int. Cl.² .................. A24B 15/027; G01N 31/14; C07G 7/02
[52] U.S. Cl. ............................. 131/266; 195/63; 195/66 R; 195/103.5 R; 195/127
[58] Field of Search .................. 195/62, 63, 65, 66 R, 195/127, 103.5 R; 131/266

[56] References Cited

U.S. PATENT DOCUMENTS 3,982,897 9/1976 Scheinberg .................. 195/63 X

*Primary Examiner*—Lionel M. Shapiro
*Attorney, Agent, or Firm*—Blum, Moscovitz, Friedman & Kaplan

[57] ABSTRACT

An enzyme referred to as carbon monoxidase and referred to hereinafter as CMase is present in red blood cells and in various bacteria and plants, including algae and fungi. The enzyme is effective for the conversion of carbon monoxide in a gas stream. Where the conversion is the step of oxidizing CO to $CO_2$, the enzyme can be used for detection of CO. The procedure lends itself to quantitative determination of CO in a gas stream. The production of CMase can be accelerated by growing bacterial cultures or plants in an atmosphere containing an increased concentration of carbon monoxide. Increasing the concentration of oxygen simultaneously is also beneficial to the process.

A filter medium including CMase can substantially decrease the concentration of carbon monoxide in a gas stream, the gas stream of particular interest being tobacco smoke. Combining the CMase in a filter with copounds which bind CO reversibly presents advantages.

47 Claims, 3 Drawing Figures

PREPARATION AND METHOD OF USE OF ENZYME EFFECTIVE FOR CONVERSION AND DETECTION OF CARBON MONOXIDE

CROSS-REFERENCE TO RELATED APPLICATIONS

This application is a continuation-in-part of my co-pending application Ser. No. 659,199, filed Feb. 19, 1976, now U.S. Pat. No. 3,982,897, entitled FILTER AND DETECTOR AND METHODS OF USING SAME IN THE REMOVAL AND DETECTION OF CARBON MONOXIDE FROM, AND IN, A GAS STREAM, itself being a continuation-in-part of my co-pending application Ser. No. 292,011, filed Sept. 25, 1972, the latter being a continuation-in-part application of my now-abandoned Ser. No. 151,153, filed June 8, 1971, and Ser. No. 102,869, filed Dec. 30, 1970, itself a continuation-in-part application of then co-pending application Ser. No. 85,087, filed Oct. 29, 1970. application Ser. No. 102,869 issued to U.S. Pat. No. 3,693,327 on Sept. 26, 1972, and application Ser. No. 85,087 was abandoned.

BACKGROUND OF THE INVENTION

In my co-pending application having the Ser. No. 659,199 and the title FILTER AND DETECTOR AND METHODS OF USING SAME IN THE REMOVAL AND DETECTION OF CARBON MONOXIDE FROM, AND IN, A GAS STREAM, I have described the fact that packed red cells can remove from a gas stream up to about four times the quantity of CO which can be accounted for on the basis of the hemoglobin present. I have attributed the unexpectedly enhanced efficacy of the composition in removal of CO from the gas stream to an enzyme, carbon monoxidase, hereinafter referred to as CMase. As will become apparent, the removal of CO from a gas stream such as tobacco smoke must be due, at least in part, to oxidation of CO to $CO_2$ by this enzyme. Moreover, the fraction of CO converted to $CO_2$ is sufficiently great so that the enzyme can be used as the basis for a device for detecting the presence of CO in a gas stream or in the ambient atmosphere.

Once the existence of an enzyme effective for the conversion of carbon monoxide was postulated, a number of previously unexplained results which had been reported in the literature immediately fell into place. One of the earliest publications pertinent to the present invention was that of Esther M. Killick in the Journal of Physiology (1948), 107, 27–44, entitled THE NATURE OF THE ACCLIMATIZATION OCCURRING DURING REPEATED EXPOSURE OF THE HUMAN SUBJECT TO ATMOSPHERES CONTAINING LOW CONCENTRATIONS OF CARBON MONOXIDE. Killick cited the results of experiments going back as far as 1856 to show that men and women whose occupation involved frequent exposure to low concentrations of CO develop a certain degree of tolerance to this gas. Experiments were also carried out by Haldane and Priestly, the results being reported in 1935. These tests also gave the same results, namely, that humans develop a degree of tolerance or acclimatization to CO.

Killick's results showed conclusively that a tolerance to CO can be developed by exposure to this gas, the tolerance being shown by a lower level of COHb in the blood of an acclimatized subject as compared with that of an unacclimatized subject, both being in equilibrium with some concentration of CO in alveolar air. Killick failed to provide a satisfactory explanation for the phenomenon, but her results are conclusive.

A. Kistner, in the Proceedings of the Section of Sciences, Koninklijke Nederlandse Akademie van Wetenschappen, Vol. LVI, Series C, 443–450 (1953), under the title "On a Bacterium Oxidizing Carbon Monoxide," provided a survey of the literature. He gives a reference to H. Kaserer, Centr. Bakt, Parasitenk. II, 16, 681, 769 (1906), who attempted to isolate hydrogen-oxidizing bacteria. He postulated the following reactions:

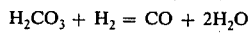

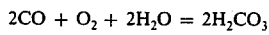

As is evident, this mechanism includes a step in which Co is oxidized by oxygen. Although the evidence was weak, Kaserer claimed the discovery of carbon monoxide oxidation by microorganisms.

C. Wehmer, in Berichte 59, 887 (1926), brought illuminating gas into contact with garden soil and observed a decrease in carbon monoxide concentration. However, there was no effect when the same test was carried out with sterilized soil. Evidently, an organism or enzyme effective for the conversion of carbon monoxide was present. Kistner actually isolated an organism from garden soil, pure cultures of which could develop in a carbon monoxide-containing atmosphere. Nevertheless, Kistner failed to carry his work forward in the direction of isolating the factor in the bacteria responsible for the conversion of CO.

E. W. Chappelle, in Biochimica Et Biophysica Acta, 62 (1962), 45–62, reported on Carbon Monoxide Oxidation by Algae. Chappelle showed that CO is oxidized to $CO_2$ in the presence of green algae and oxygen and that the rate is increased several-fold in the presence of light.

As is evident from the above citations, the ability to convert CO, generally to $CO_2$, is present in mammals, plants and bacteria. This is reasonable from the standpoint of evolution, since CO is ubiquitous, and it is likely that this ability is even more widespread, being present in many species of both plant and animal phyla.

The capacity to cope with CO, as noted in my co-pending application, almost certainly stems from the fact that the atmosphere contains a small but by no means negligible quantity of CO. Significantly, although this capacity for converting CO has been recognized in mammals, bacteria and plants, it has not been recognized that there may be a specific factor or factors responsible for the conversion and that isolation of such a factor or factors may be of value for the removal and detection of CO from ambient atmosphere or from gas streams. Further, while in my co-pending application, I have taught how the factor present in mammalian blood may be utilized, note is taken of the fact that utilization of mammalian blood for the purposes specified may not represent the most economic means of reaching the stated objectives. Consequently, there is value in establishing processes for isolation and utilization of such a factor or factors when derived from bacteria and from plants, as well as from blood, the term "plants" herein being taken to include algae and fungi.

SUMMARY OF THE INVENTION

In accordance with the present invention, a factor or enzyme termed carbon monoxidase or CMase is derived from blood, bacteria and plants in which this enzyme is widely distributed. It is recognized that the composition or structure of CMase will vary with the source thereof. Consequently, the term "CMase" is to be regarded as defining a class of enzymes functionally rather than structurally. The enzyme in a form suitable for use for conversion of carbon monoxide or detection thereof can be utilized as a component of the whole organism or it can be isolated from the bacterium or plant following rupture of the cell wall. The cell wall can be ruptured by sonication, lyophilization or osmotic shock. The resulting suspension can be centrifuged into soluble and insoluble fractions and the location of the CMase in either, or both, determined. When appreciable concentrations of the enzyme are in the insoluble fraction, solubilization as with nonionic detergents is achieved. The fraction containing the soluble enzyme is then subjected to standard protein fractionation procedures. After fractionation, the protein can be adsorbed on a support such as charcoal, cellulose or Sepharose and similar gels, to form a filter.

The concentration of the enzyme in a bacterium or in a specific plant can be increased by culturing the bacterium or growing the plant in an atmosphere containing higher than normal concentrations of CO and $O_2$. The partial pressures of these two gases may exceed normal atmospheric pressure, the process being carried out in a pressure vessel.

The enzyme, either unpurified or purified to the extent desired, may be adsorbed, as aforenoted, on a suitable substrate. Alternatively, it may be used in solution. Whether used in solution or as a solid, it may be combined with a compound such as hemoglobin or microperoxidase, both of these compounds containing active heme groups linked to a polypeptide. The advantage of combining hemoglobin with the enzyme is that hemoglobin can hold both CO and $O_2$, and the close proximity of the CO and the $O_2$ on the hemoglobin facilitates the catalytic conversion of the CO. Where hemoglobin is used in combination with the enzyme, it is desirable to provide a reductant effective for preventing the conversion of hemoglobin to methemoglobin and similarly for other heme-polypeptides. The ratio of equivalents of reductant to hemoglobin should lie in the range from 1 to 8. It is also desirable that a buffer be present when the hemoglobin and the enzyme are in solution, the buffer being selected to maintain the pH between 6.0 and 8.5. Suitable buffers are the phosphate buffers and tris(hydroxymethyl) aminoethane-HCl.

The enzyme can be used for detecting CO in a gas stream or in the ambient atmosphere as well as for converting CO. The detection process depends on converting the CO to $CO_2$, which is then absorbed in a material such as lime. Where the conversion to $CO_2$ is quantitative, as is usually the case, the enzyme can be used for quantitative determination of the CO in a gas stream.

Accordingly, an object of the present invention is a process for obtaining and utilizing an enzyme active for the conversion of carbon monoxide from blood, a bacterium or a plant.

Another object of the present invention is a process for the purification of said enzyme to a desired degree.

A further object of the present invention is a process for the detection of carbon moxoxide in a gas stream or an ambient atmosphere.

An important object of the present invention is a filter for reduction of the quantity of carbon monoxide in a gas stream.

A significant object of the present invention is a filter for the conversion of carbon monoxide in tobacco smoke.

Yet another object of the present invention is a composition containing an enzyme effective for conversion of carbon monoxide.

Yet a further object of the present invention is a composition containing an enzyme effective for the conversion of carbon monoxide bound to a compound which holds carbon monoxide reversibly.

Still other objects and advantages of the invention will in part be obvious and will in part be apparent from the specification.

The invention accordingly comprises the several steps and the relation of one or more of such steps with respect to each of the others; the apparatus embodying features of construction, combinations and arrangement of parts which are adapted to effect such steps; and the product which possesses the characteristics, properties, and relation of constituents, all as exemplified in the detailed disclosure hereinafter set forth, and the scope of the invention will be indicated in the claims.

BRIEF DESCRIPTION OF THE DRAWING

For a fuller understanding of the invention, reference is had to the following description taken in connection with the accompanying drawing, in which.

DESCRIPTION OF THE PREFERRED EMBODIMENTS

Figure 1:
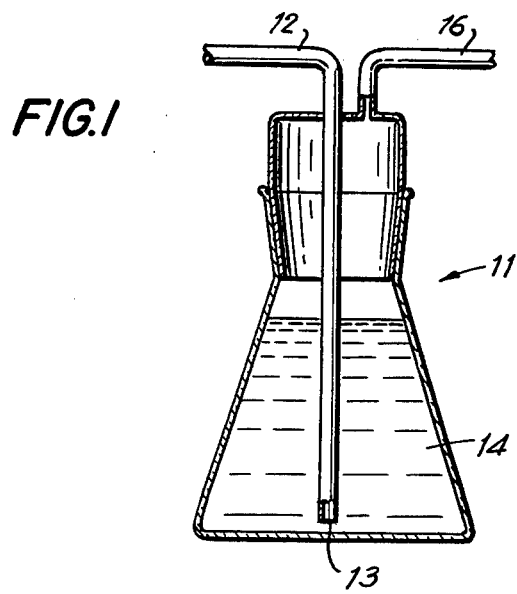
FIG. 1 is a hookah-like device for the absorption of CO from a gas stream.

Generally speaking, the enzyme CMase, effective for conversion of CO and, in particular, for oxidizing CO to $CO_2$, is present in blood and in a wide variety of bacteria and plants, as aforenoted. Specific examples of bacteria from which the enzyme can be obtained are the following:

*Methanosarcina barkerii*
*Methanobacterium formicicum*
*Bacillus oligocarbophillus* (hydrogenomonas carboxydovorans)
*Desulfovibrio desulfuricans*

Specific plants from which CMase can be obtained are:

*Chlorella vulgaris*
Scenedesmus
Spinach and cucumber leaves

The following example illustrates the method of obtaining CMase from Hydrogenomonas carboxydovorans, a Gram-negative, monotrichously flagellated rod-shaped bacterium. To isolate a culture which produces CMase, two grams of sewage sludge were inoculated into, for instance, 200 ml of a medium containing 0.2% $KNO_3$, 0.1% $K_2HPO_4$ and 0.01% $MgSO_4 . 7H_2O$, adjusting the pH to 7.2. The sludge culture was grown in an atmosphere containing 30% CO, 20% $O_2$ and 50% $N_2$, yielding an organism that could oxidize CO to $CO_2$. The culture contained at least six different types of bacteria, as became evident when they were studied morphologically after streaking them out and culturing them on a solid medium, that is, the solution as described above, plus an enrichment of 1% sterilized sewage sludge, plus 2% agar. A culture of these six organisms was then grown in liquid media of the type described and enriched, but under an atmosphere of 70% CO, 20% $O_2$ and 10% $N_2$. A pure culture of a single type of bacterium, namely, hydrogenomonas carboxydovorans, resulted. Apparently, the nonspecific organisms were killed by the relatively high concentration of CO.

The enzyme CMase is inducible, since it is produced when the organism is grown under a high CO concentration, such as at 30%. Nonspecific, presumably non-CMase-producing bacteria also grow at concentrations as high as 30%, but the latter are killed off at concentrations substantially higher than 30%, such as at 70% CO, leaving a pure culture of the CMase-producing bacterium.

The rate of production of CMase may be increased by increasing the partial pressure of CO, provided that the concentration of $O_2$ does not become limiting. Under the latter circumstance, it is desirable that the partial pressure of $O_2$ also be increased. As is evident, the partial pressures of CO and $O_2$ can be increased to the point where the sum of the partial pressures is greater than atmospheric, in which case a pressure vessel must be used. The upper pressure limit is reached either when the rate of production of the enzyme levels off or when it becomes uneconomical to reinforce the pressure vessel.

The enzyme may be concentrated, if desired, following fragmentation of the cells, as by lyophilization, sonication or osmotic shock. The resulting suspension is separated into soluble and insoluble fractions, as by centrifugation, and the fractions analyzed to determine the location of the desired enzyme. Should there be an appreciable, or the major, concentration of the enzyme in the insoluble fraction, solubilization, with such reagents as nonionic detergents, is effected.

The solution containing CMase is then subjected to standard protein fractionation procedures, such procedures being appropriate, since the enzyme is a protein. Examples of such procedures are ethanol fractionation, with control of ionic composition, temperature, pH and protein and ethanol concentration; precipitation with heavy metals, such as zinc; and chromatographic separation using appropriate adsorbents. Examples of such adsorbents are Sepharose, Sephadex, made by Pharmacia, anion exchange resins such as those made by Dow Chemical Company, Diamond-Shamrock, Rohm and Haas Company, and the Permutit companies of England and the U.S.A. Further examples are the cationic exchange resins made by the same companies, macroporous resins and mixed bed resins also made by the same companies. Other suitable absorbents are the ion exchange celluloses sold by Bio-Rad Laboratories. Among the cellulosic materials are those manufactured from high-purity cotton having an alpha-cellulose content of about 98%, fibrous cellulose powders and microgranular powders. The Sepharose and Sephadex absorbents are examples of a wide variety of gels which also are effective for chromatographic separation of proteins.

The foregoing process is also adaptable for the production of the desired enzyme from plants, including algae and fungi. As is obvious, the plants can be fragmented by processes such as maceration, high-speed grinding, etc. Also, growing the plants in high concentrations of CO and, optionally, high concentrations of oxygen can increase the rate of production of the enzyme.

To obtain CMase from blood, the red blood cells are subjected to lysis and the ghosts are separated off. Hemoglobin is precipitated from the supernatant by addition of ammonium sulphate to bring the concentration thereof to 45% to 55% of saturation, maintaining the pH above 6.0, and the hemoglobin is removed. The supernatant is dialyzed against 0.01 molar ammonium acetate to remove the ammonium sulphate while buffering the supernatant. The solution is tested for CMase by passing a gas stream containing CO and $O_2$ therethrough and analyzing for extent of removal of CO.

To test the ghosts for CMase bound thereto, they are fragmented as by sonication or osmotic shock and treated with detergent to solubilize any CMase held in the membranes. The resultant solution is tested as above. The CMase can be obtained as a dried powder by freeze-drying, with the additional advantages that the amonium acetate maintains the solution close to neutrality during the process and is itself removed by sublimation.

While it is preferable that the enzyme be concentrated for use either in the conversion of CO or in the detection of CO, a composition containing the intact or disrupted blood cells, bacteria or plant may be used as such, but preferably in combination with a carrier. Thus, the whole bacteria may be lyophilized and the resulting dry powder utilized by itself as a filter medium. When the lyophilized bacteria are used as a filter medium, the filter may be preceded in the filter train by water, or a suitable solvent, to provide the necessary water vapor to allow the enzyme to react with carbon monoxide. Alternatively, the stream of gas or smoke may be supplied with water vapor sufficient for the purpose.

Also, as aforenoted, the concentrated or the purified enzyme, derived as described above, may also be lyophilized and used as the filter medium in a similar fashion. Preferably, however, the enzyme is used on a support of the type described. Additional supports are activated charcoal and Rohm and Haas IR-120 and IRA-400. Carbo-resin has also been found to be a satisfactory support.

Where the enzymes (carbon monoxidases) are derived from plants, they can also be used as the whole organism, or where the concentration of enzyme therein is insufficient, as preparations which are prepared by fractionation by the techniques described in connection with derivation of such enzymes from bacteria.

A particularly suitable substrate to be used in combination with the enzyme is a material which can reversibly bind CO and $O_2$. In general, these are compounds with structures including one or more heme moieties joined to a polypeptide chain. Examples are ferrous hemoglobin and so-called microperoxidase. Microperoxidase is a heme-polypeptide or heme-peptide which can be obtained by digestion of cytochrome c with pepsin in a procedure modified from that of Tuppy and Paléus (Acta Chem. Scand. 9 353 1955). It has a molecular weight of about 1900, whereas hemoglobin has an equivalent weight of 16,500. Consequently, on an equal weight basis, it can bind almost 9 times as great a quantity of CO. Moreover, although the binding is reversible, the tightness of binding is much greater than is the case with hemoglobin. Therefore, it is far superior to hemoglobin on a stoichiometric basis and also with respect to the equilibrium concentration in a gas stream to which CO can be dropped by its use in a filter.

Significantly, heme itself is not nearly so active as hemoglobin or microperoxidase in binding CO. Consequently, although its molecular weight is only 616.5, it cannot be used to replace the heme-polypeptides.

The use of a heme-polypeptide as substrate will serve not only to increase the surface of the enzyme accessible to CO, but will also serve to trap both CO and $O_2$, thereby bringing together both reactants required by the CMase. Moreover, it will prolong the contact between the two reactants and the catalytic enzyme. In view of the fact, however, that ferrous hemoglobin, especially during processing, may be converted to methemoglobin, it is desirable that a reductant such as ascorbic acid, methylene white or dithionite ion be present. Preferably, the ratio of reductant to hemoglobin, expressed in equivalents, should lie in the range from 1 to 8. Also, a buffer such as a phosphate buffer or a tris(hydroxymethyl)aminoethane-HCl buffer should be present in an amount to hold the pH of the composition between 6.0 and 8.5, especially where the composition is in solution. It is also preferable to use a reductant and buffer with other heme-polypeptide compounds which can bind CO and $O_2$.

An absorber in which the enzyme, either by itself or in combination with a heme-polypeptide, can be used effectively is shown in FIG. 1. The gas stream from which CO is to be removed, either entirely or in part, is introduced into absorption flask 11 through inlet tube 12 and inlet tip 13 into solution 14. The gas exits from absorber 11 through exit tube 16. To avoid inconvenient foaming, it is advisable to add a small quantity, usually a few drops, of an anti-foaming agent such as methylsilicone or octyl alcohol. Where a heme-polypeptide is present in the solution, it is preferable that a reductant as aforenoted be incorporated in the solution, together with a buffer. The reductant should be effective for preventing the conversion of the ferrous heme-protein by any oxygen present. Moreover, the reducing agent should be of such a type that it can function when the pH of the solution is within the range in which the heme-polypeptide is active, since the heme-polypeptide may be denatured at pHs significantly outside this range. For hemoglobin, the range is 6.0-8.5. It should be noted that where the solution is traversed by hot smoke, the reducing agent should be such that it cannot give rise to volatile toxic products, since it would then be inadvisable for use where the smoke is to be inhaled. However, as is evident, such a reducing agent can be used in a test procedure or in an analytical procedure.

To summarize the requirements of an effective reductant, it must be one which can maintain the heme-polypeptide in its active state in the presence of oxygen until said reductant is exhausted; it must not interfere with the activites of the enzyme or heme-polypeptide or other factors towards CO; and it must not introduce undesirable contaminants into a gas stream passing therethrough when the stream is to be inhaled.

Figure 2:
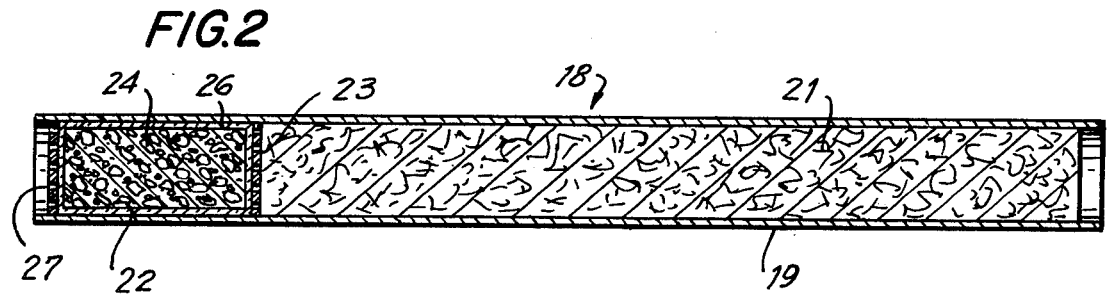
FIG. 2 is a sectional view of a cigarette incorporating a filter on which is a composition including an enzyme effective for conversion of CO in tobacco smoke.

It should be noted that a heme-polypeptide and particularly microperoxidase can be used in a solution or on a solid substrate without CMase. Where used in this way, the capacity of a filter based on the polypeptide alone for removal of CO will be limited by the stoichiometry of the compound, whereas CMase, functioning as a catalyst, can provide theoretically unlimited conversion of CO.

Where it is desired to remove carbon monoxide from tobacco smoke without using a solution in an absorber as shown in FIG. 1, the cellular material may be made up into a filter to be placed in the mouthpiece of a cigarette, cigar or pipe. One form of such a filter is shown in FIG. 2, in which a cigarette is represented generally by the reference numeral 18, the cigarette comprising a cigarette paper 19 containing tobacco 21 at the distal end thereof and a filter cartridge 22 in the mouthpiece of the cigarette, the filter 22 and the charge of tobacco 21 being separated by a permeable or perforated barrier 23. The filter charge 24 contains a CMase either by itself or in combination with a heme-polypeptide and/or on an absorbent material such as cellulose floc, activated carbon or one of the aforenoted adsorbents. The purpose of using such a solid absorbent, of course, is to facilitate transit of tobacco smoke therethrough. The term "tobacco smoke" is used generically to include both the gas stream leaving the burning tobacco and the particulate matter therein.

Where the filter contains hemoglobin as well as CMase, it is preferable that the filter charge also incorporate from 1 to 8 equivalents of an effective reductant per equivalent of hemoglobin in the charge. Further, it is preferable that a buffer capable of maintaining the pH between 6.0 and 8.5 also be present in the charge, the buffer and the reductant being of such a type that they will not adversely affect the activity of the CMase or the hemoglobin or generate toxic volatile substances into the gas stream.

For protection of the CMase and, particularly, where accompanied by a heme-polypeptide, in filter 22 during storage of cigarettes fitted with such filters, the charge can be encapsulated in a frangible container 26 as shown in FIG. 2. The container should be of a material such that it can be readily broken between the fingers. Alternatively, the container could have a tip (not shown) which can easily be broken off. An additional filter 27, which serves to prevent any glass shards or the like from being inhaled with the gas stream by the smoker, may also be incorporated in the cigarette.

As is evident, a similar arrangement can be used for cigars. Alternatively, an absorber such as is shown in FIG. 1 and indicated by the reference numeral 11 may be used in combination with an ordinary cigarette (minus filter 22) or a cigar or a pipe. Another possibility is a pipe (not shown) with a stem so constructed that a filter can be inserted therein as an accompaniment to filling the pipe with a fresh charge of tobacco. Where the filter contains hemoglobin or another heme-polypeptide, deterioration may be prevented or at least delayed by storing the composition under refrigeration.

The terms "absorb," "absorber" and "conversion" as used herein with respect to the effect of CMase on CO in a gas are to be understood as encompassing any process which decreases the concentration of CO in said gas, whether the CMase functions by catalysis of a reaction or by any other means.

Figure 3:
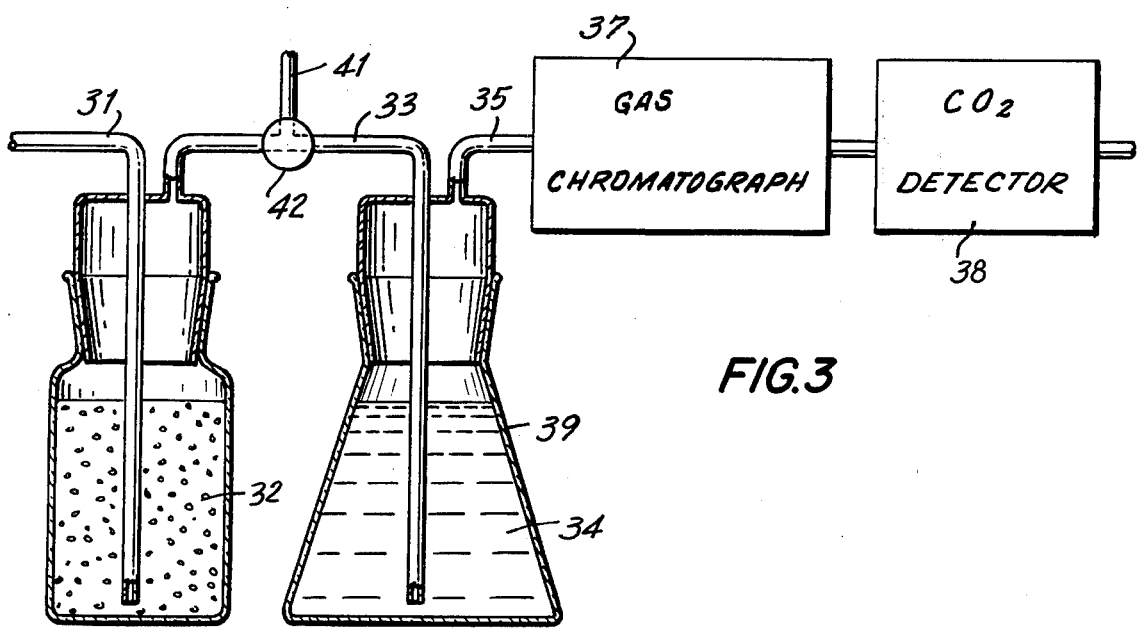
FIG. 3 is an apparatus for determining carbon monoxide in ambient air or a gas stream.

The oxidation of CO to $CO_2$ by CMase in the presence of oxygen makes it possible to use the enzyme for the detection, quantitatively if desired, of CO in a gas. FIG. 3 illustrates apparatus appropriate for this purpose. The gas is introduced by appropriate means (not shown) through inlet tube 31 into $CO_2$-absorber 32 and then through conduit 33 into CO-conversion solution 34, which contains CMase. The CMase composition 34 is now viewed as a reagent for catalyzing the conversion of CO to $CO_2$ by the $O_2$ in the gas stream. The gas stream, now carrying any $CO_2$ produced by oxidation of CO in the gas stream, is carried through exit tube 35 through an appropriate CO detector represented schematically by box 38. Optionally, a gas chromatograph 37 may be positioned between gas converter 39 and the $CO_2$ detector. The gas chromatograph can serve to determine whether carbon monoxide is still present in the gas stream.

For quantitative determination of the extent of conversion, the $CO_2$ detector may be a weighing bottle containing any of the conventional $CO_2$ absorption reagents, such as CaO. Alternatively, the gas stream leaving absorber-converter 39 can be led into lime water to produce visible calcium carbonate. Where the gas stream to be analyzed is initially free of $CO_2$, the stream can be introduced into flask 39 through entrance tube 41 and three-way stop-cock 42.

It has already been noted that there is an advantage to combining a heme-polypeptide such as hemoglobin with CMase in order to hold CO and $O_2$ in closer contact with the CMase and for a longer period of time than would otherwise be the case. This concept can be utilized in another way. Tests have shown that a smoker normally inhales about 30 ml of tobacco smoke with each puff, and that there is an interval of a substantial number of seconds between puffs. The same is true for cigar and pipe smokers. In order to increase the holding time of the tobacco smoke in contact with the CMase, the filter charge 24 may have a gross volume at least equal to the volume of a normal puff of smoke, that is, at least 30 ml. As a result, each puff on the cigarette will draw in that volume of gas which has been in contact with the filter charge 24 for the number of seconds constituting the interval between puffs; simultaneously, a new puff volume of tobacco smoke will be brought into the filter charge 24 to remain there for the duration of the interval between puffs. Thus, expanding the volume of the filter charge to at least that of a normal puff greatly increases the time of contact between CO and $O_2$ with the enzyme, and facilitates approach to quantitative conversion of the CO to the final reaction product. Needless to say, the filter charge need not be in the shape shown in FIG. 2. For instance, the shape of absorber-converter 11 may be such that bubbles of gas travel upward slowly through the solution of CMase, the time of transit through the CMase being extended to increase the duration of contact of the gas with the CMase and thus promote complete conversion. Where the volume of gas in transit through the solution is equivalent to that of a normal puff, then the effect will be exactly the same as that achieved by the cartridge of FIG. 2.

It will thus be seen that the objects set forth above, among those made apparent from the preceding description, are efficiently attained, and since certain changes may be made in carrying out the above process, in the described product, and in the constructions set forth without departing from the spirit and scope of the invention, it is intended that all matter contained in the above description and shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A filter for the conversion and detection of CO in a gas stream, comprising a container suitable for transit of a gas stream therethrough and a composition including enzyme carbon monoxidase, hereinafter referred to as CMase.

2. The filter as claimed in claim 1, wherein said CMase is a product derived from red blood cells.

3. The filter as claimed in claim 1, wherein said CMase is a product derived from bacteria.

4. The filter as claimed in claim 1, wherein said CMase is a product derived from a plant, the term "plant" being taken to include algae and fungi.

5. The filter as claimed in claim 1, wherein said composition includes a heme-polypeptide intermixed with said CMase.

6. The filter as claimed in claim 5, wherein said heme-polypeptide is ferrous hemoglobin.

7. The filter as claimed in claim 6, wherein said composition further includes a reductant effective for preventing the conversion of ferrous hemoglobin to methemoglobin in the presence of oxygen.

8. The filter as claimed in claim 7, wherein the ratio of the number of equivalents of said reductant to the number of equivalents of said ferrous hemoglobin is between 1 and 8.

9. The filter as claimed in claim 7, wherein said reductant is selected from the group consisting of ascorbic acid, methylene white and dithionite ion.

10. The filter as claimed in claim 5, wherein said heme-polypeptide is microperoxidase.

11. The filter as claimed in claim 1, wherein said composition is in solution.

12. The filter as claimed in claim 11, wherein said composition includes an antifoaming agent.

13. The filter as claimed in claim 11, wherein said composition includes a reductant effective for preventing the conversion of ferrous hemoglobin to methemoglobin in the presence of oxygen, and a buffer for holding the pH of said solution between about 6.0 and 8.5.

14. The filter as claimed in claim 1, wherein said filter is part of a smoking device.

15. The filter as claimed in claim 14, wherein the volume of said filter is at least equal to the volume of a normal puff of smoke.

16. The filter as claimed in claim 1, wherein said container includes a frangible member for protecting said composition prior to putting said filter into use.

17. The filter as claimed in claim 1, wherein said CMase is included in a liquid culture of bacteria.

18. The filter as claimed in claim 1, wherein said CMase is a portion of a culture of bacteria on a solid medium.

19. The filter as claimed in claim 18, wherein said solid medium is a gel.

20. The filter as claimed in claim 18, wherein said solid medium is a member of the group consisting of Sepharose, Sephadex, anionic exchange resins, cationic exchange resins, powdered cellulose, fibrous cellulose, Carbo-resin and microgranular cellulose.

21. The filter as claimed in claim 1, further comprising means for removing $CO_2$ from said gas stream prior to entry of said gas stream into said container, and means for detecting $CO_2$ in said gas stream leaving said container, said CMase having the property of converting CO to $CO_2$ in the presence of $O_2$.

22. The filter as claimed in claim 21, wherein said means for detecting $CO_2$ is a weighed container containing an oxide convertible to a carbonate in contact with $CO_2$.

23. A composition effective for conversion of CO, comprising an effective amount of enzyme carbon monoxidase, hereinafter referred to as CMase, and a carrier.

24. The composition as claimed in claim 23, wherein said CMase is a product derived from red blood cells.

25. The composition as claimed in claim 23, wherein said CMase is a product derived from bacteria.

26. The composition as claimed in claim 23, wherein said CMase is a product derived from a plant, the term "plant" being taken to include algae and fungi.

27. The composition as claimed in claim 23, wherein said composition further comprises a heme-polypeptide intermixed with said CMase.

28. The composition as claimed in claim 27, wherein said heme-polypeptide is microperoxidase.

29. The composition as claimed in claim 27, wherein said heme-polypeptide is ferrous hemoglobin.

30. The composition as claimed in claim 29, wherein said composition further includes a reductant effective for preventing the conversion of ferrous hemoglobin to methemoglobin in the presence of oxygen.

31. The composition as claimed in claim 30, wherein the ratio of the number of equivalents of said reductant to the number of equivalents of said ferrous hemoglobin is between 1 and 8.

32. The composition as claimed in claim 30, wherein said reductant is selected from the group consisting of ascorbic acid, methylene white and dithionite ion.

33. The composition as claimed in claim 23, wherein said composition is in solution.

34. The composition as claimed in claim 33, wherein said composition includes an antifoaming agent.

35. The composition as claimed in claim 33, wherein said composition includes a reductant effective for preventing the conversion of ferrous hemoglobin to methemoglobin in the presence of oxygen, and a buffer for holding the pH of said solution between about 6.0 and 8.5.

36. A process for the production and purification of enzyme carbon monoxidase, hereinafter termed CMase, comprising the steps of selecting a member of the group consisting of red blood cells, CMase-producing bacteria and CMase-producing plants, the term "plants" including algae and fungi, suspending said member in water, fragmenting said member, separating said fragmented member into soluble and insoluble fractions, determining whether said CMase is present in said soluble or in said insoluble fraction, and isolating said CMase from the fraction containing same.

37. The process as defined in claim 36, wherein said member is a CMase-producing bacterium in the form of a liquid bacterial culture and further comprising the steps of concentrating said culture by centrifugation prior to fragmenting said member.

38. The process as defined in claim 36, wherein said fragmentation is carried out by lyophilization, sonication or osmotic shock.

39. The process as defined in claim 36, wherein said bacteria are selected from the group consisting of *Methanosarcina barkerii, Methanobacterium formicicum, Bacillus oligocarbophillus (Hydrogenomonas carboxydovorans),* and *Desulfovibrio desulfuricans.*

40. The process as defined in claim 36, wherein said bacteria are those of the *Bacillus oligocarbophillus (Hydrogenomonas carboxydovorans).*

41. The process as defined in claim 36, further comprising the step of adding an effective amount of a solubilizing agent to said insoluble fraction in the event said CMase is in said insoluble fraction.

42. The process as defined in claim 41, wherein said solubilizing agent is a detergent.

43. The process as defined in claim 36, wherein said step of isolating said CMase is effected by a member of the group consisting of ethanol fractionation, with control of ionic composition, temperature, pH, and ethanol and protein concentration; precipitation with heavy metals; and chromatographic separation.

44. The process as defined in claim 43, wherein said chromatographic separation is effected using a member of the group of selective absorbents consisting of Sepharose, Sephadex, anionic exchange resins, cationic exchange resins, Carbo-resin, powdered cellulose, fibrous cellulose and microgranular cellulose.

45. The process as defined in claim 37, wherein said bacteral culture is grown in an atmosphere containing a concentration of carbon monoxide greater than normally present in air.

46. The process as defined in claim 45, wherein said bacterial culture is grown in an atmosphere in which the partial pressures of carbon monoxide and oxygen are greater than obtain in normal air, the upper limit of said partial pressures being set by those pressures at which essentially no increase in the rate of growth of said bacteria takes place and by the pressure at which it becomes uneconomical to construct adequately strong pressure vessels.

47. The process as defined in claim 37, wherein said bacterium has the name hydrogenomonas carboxydovorans and said culture is produced by inoculating sewage sludge into a medium in the ratio of 1 gram to 100 ml, said medium containing approximately 0.2% $KNO_3$, 0.1% $K_2HPO_4$, 0.01% $MgSO_4 \cdot 7H_2O$, and adjusting the pH to 7.2.

* * * * *